US005769079A

United States Patent [19]
Hossack

[11] Patent Number: 5,769,079
[45] Date of Patent: Jun. 23, 1998

[54] METHOD AND APPARATUS FOR DETERMINING QUANTITATIVE MEASURES OF FLOW PARAMETERS

[75] Inventor: John A. Hossack, Palo Alto, Calif.

[73] Assignee: Acuson Corporation, Mountian View, Calif.

[21] Appl. No.: 736,048

[22] Filed: Oct. 22, 1996

[51] Int. Cl.[6] .................................................... A61B 8/00
[52] U.S. Cl. ..................................................... 128/661.08
[58] Field of Search ........................ 128/661.08, 661.09, 128/661.1; 73/861.25, 861.26

[56] References Cited

U.S. PATENT DOCUMENTS

| | | |
|---|---|---|
| 4,265,126 | 5/1981 | Papadofrangakis et al. . |
| 4,759,375 | 7/1988 | Namekawa . |
| 4,819,650 | 4/1989 | Goldstein . |
| 5,000,184 | 3/1991 | Bonnefous . |
| 5,186,176 | 2/1993 | Hiki et al. . |
| 5,222,393 | 6/1993 | Phillips et al. . |
| 5,375,600 | 12/1994 | Melton . |
| 5,390,677 | 2/1995 | Ferrera et al. . |
| 5,398,216 | 3/1995 | Hall et al. . |
| 5,409,010 | 4/1995 | Beach et al. . |
| 5,443,071 | 8/1995 | Banjanin et al. . |
| 5,505,204 | 4/1996 | Picot et al. . |
| 5,515,857 | 5/1996 | Tsujino et al. . |
| 5,555,886 | 9/1996 | Weng et al. . |
| 5,562,098 | 10/1996 | Lerner . |
| 5,566,674 | 10/1996 | Weng . |

OTHER PUBLICATIONS

Ding–Yu Fei et al., "Angle Independent Doppler Color Imaging: Determination of Accuracy and a Method of Display", *Ultrasound in Med. & Biol.*, vol. 20, No. 2, pp. 147–155, 1994.

Patent application for Ultrasound System for Flow Measurement; J. Nelson Wright et al., Serial No. 08/432,858, filed May 2, 1995.

*Primary Examiner*—Marvin M. Lateef
*Assistant Examiner*—Derrick Fields
*Attorney, Agent, or Firm*—Brinks Hofer Gilson & Lione

[57] ABSTRACT

A method for making Doppler ultrasound measurements utilizes an ultrasound probe having two transducer arrays oriented at right angles to one another and spaced apart from one another. The first array is used to measure multiple apparent Doppler parameters such as velocity at respective regions within a cross section of a structure such as a blood vessel. The second array is used to measure second apparent Doppler parameters at one of these regions. The first and second apparent Doppler parameters for the same point are used to correct the first apparent Doppler parameters to more nearly equal true velocity or energy.

9 Claims, 5 Drawing Sheets

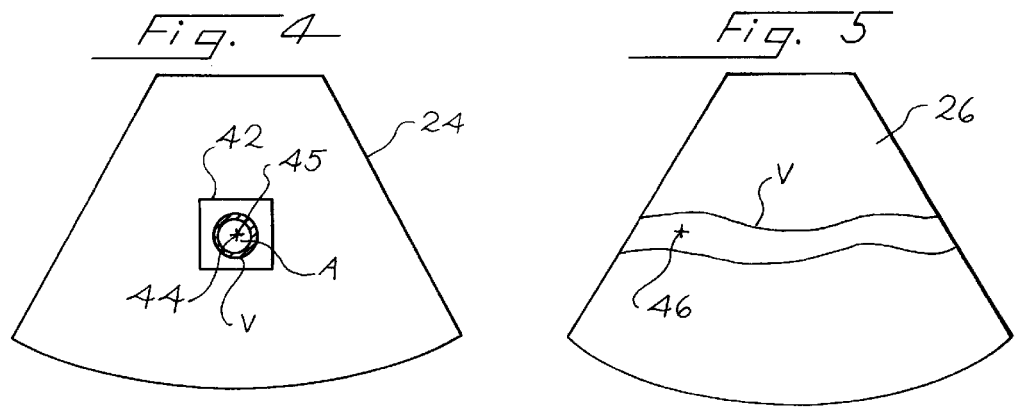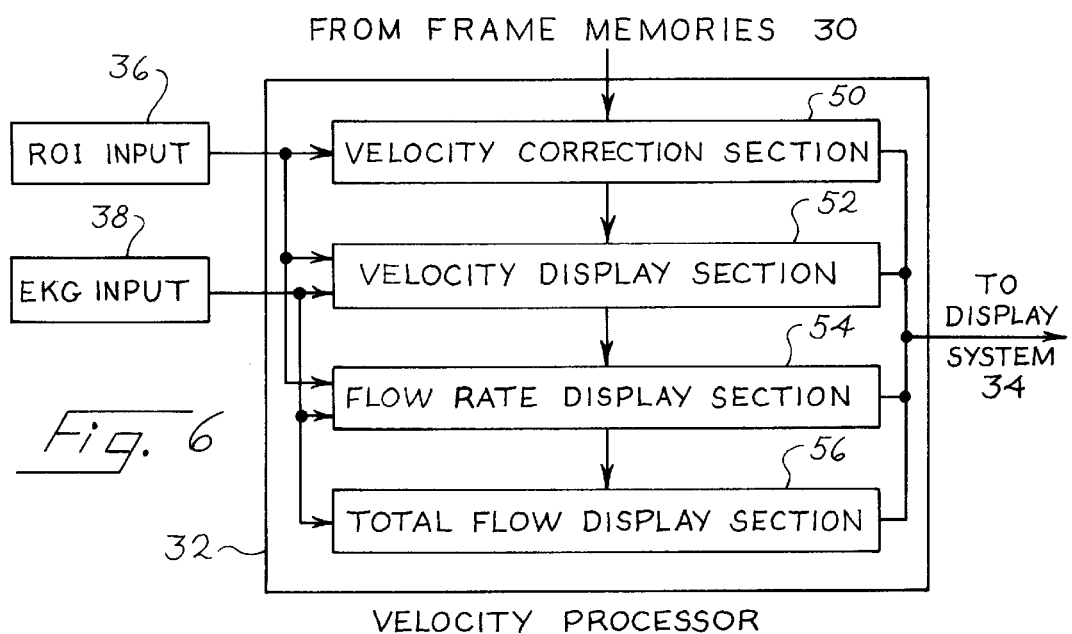

METHOD AND APPARATUS FOR DETERMINING QUANTITATIVE MEASURES OF FLOW PARAMETERS

BACKGROUND OF THE INVENTION

This invention relates to the field of Doppler ultrasound measurements, and in particular to improved systems for providing quantitative measures of various Doppler flow parameters.

Doppler ultrasound systems have been used to measure velocities, flow rates and stroke volumes in medical imaging applications. For example, Picot U.S. Pat. No. 5,505,204 discloses the use of an ultrasound transducer having a position/orientation sensor on the transducer. The disclosed system utilizes the known position and orientation of the transducer to compensate for systematic errors in apparent Doppler velocity. In particular, Doppler measurements of velocity respond only to the velocity component aligned with the ultrasonic scan line along which the velocity measurement is taken, and the flow velocity is generally not parallel with the interrogating scan line. Picot also discusses the integration of corrected velocity over an area such as the cross-sectional area of a blood vessel to find the total flow rate of blood within the vessel.

Tsujino U.S. Pat. No. 5,515,857 discloses an ultrasonic Doppler system for estimating blood flow velocity, blood flow rate and stroke volume. In Tsujino multiple angled observations of Doppler velocity are averaged to provide an improved estimate of the actual velocity.

Another method for correcting apparent Doppler velocity to arrive at a better estimate of true velocity includes the use of an operator-supplied input value to estimate the Doppler angle between the interrogating scan line and the actual flow velocity. This method is cumbersome and susceptible to human error.

Another prior art approach estimates velocity based on a frame-to-frame correlation of blood speckle. This approach avoids the Doppler angle problem, but requires substantial computation, and it estimates velocity based only on components of the velocity in the scan plane.

SUMMARY OF THE INVENTION

The present invention is directed to an improved method and apparatus that allow rapid and effective correction of Doppler parameters to account for the Doppler angle between the actual flow and the interrogating scan line.

According to this invention, a method is provided for making Doppler ultrasound measurements. This method includes the step of providing an ultrasound probe comprising first and second transducer arrays, each array comprising a respective plurality of transducer elements and a central image plane. The central image planes are oriented to intersect at an angle greater than 45°, and the arrays are spaced from one another. The first transducer array is used to measure a plurality of first apparent Doppler parameters at a respective plurality of regions within a cross-section of a structure, and the second transducer array is used to measure a second apparent Doppler parameter substantially at one of the regions.

The second apparent Doppler parameter is preferably used to correct at least some of the first apparent Doppler parameters, for example to provide an improved estimate of the actual velocity. Once the first apparent Doppler parameters have been corrected, they can be processed to provide various flow measures, such as velocities, flow rates and stroke volumes.

BRIEF DESCRIPTION OF THE DRAWINGS

FIGS. 4 and 5 are images generated with the first and second transducer arrays of FIG. 1, respectively.

FIG. 6 is a more detailed block diagram of the velocity processor of FIG. 1.

FIG. 7 is a schematic view of a display generated by the velocity processor of FIG. 1.

DETAILED DESCRIPTION OF THE PRESENTLY PREFERRED EMBODIMENTS

Figure 1:
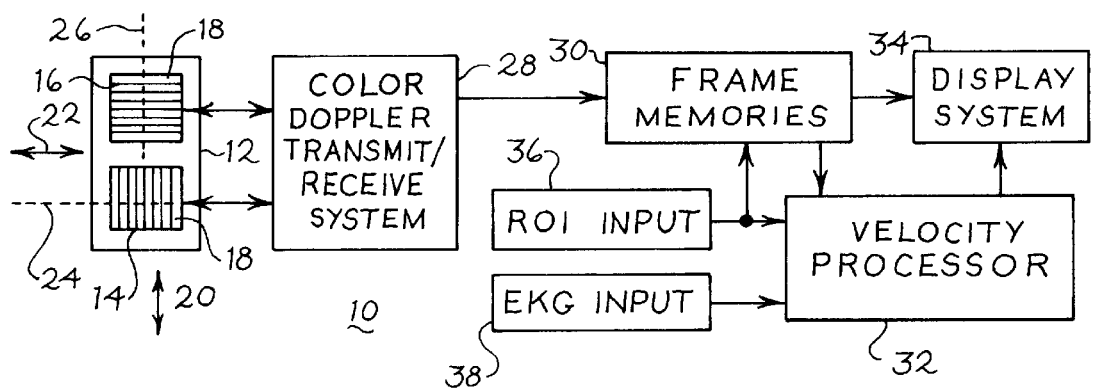
FIG. 1 is a block diagram of an ultrasound imaging system that incorporates a presently preferred embodiment of this invention.

Turning now to the drawings, FIG. 1 shows an ultrasonic imaging system 10 which incorporates a presently preferred embodiment of this invention.

The imaging system 10 includes an ultrasonic probe 12 which includes two separate transducer arrays 14, 16 that are rigidly mounted with respect to one another. Each of the transducer arrays 14, 16 includes a respective array of transducer elements 18. The transducer elements 18 of the first transducer array 14 are each longer than wide, and are oriented with their length dimension parallel to an element axis 20. Similarly, the transducer elements 18 of the second transducer array 16 are also oriented parallel to one another, with their length dimension parallel to an element axis 22. As shown in FIG. 1, the elements of the first transducer array 14 are arranged perpendicular to and coplanar with the elements of the second transducer array 18 in this embodiment.

When operated as a conventional phased array each of the transducer arrays 14, 16 forms a scan plane along a respective central image plane 24, 26. The central image plane 24 of the first transducer array 14 is perpendicular to the element axis 20, and the central image plane 26 of the second transducer array 16 is perpendicular to the element axis 22. Preferably, the angle between the central image planes 24, 26 is greater than 45°. Most preferably, the central image plane 24 is perpendicular to the central image plane 26. In a situation where an array is not steerable in elevation and therefore always uses a single scan plane, this single scan plane will be referred to as the central scan plane here.

The imaging system 10 also includes a color Doppler transmit/receive system 28 that operates in the conventional manner to supply beamformed transmit signals to the transducer arrays 14, 16 and to beamform receive signals generated by the transducer arrays 14, 16 to form Doppler measurement signals at multiple points in the respective central image planes 24, 26.

Color Doppler transmit/receive systems are well known to those skilled in the art, and will not therefore be described in any detail here. The system 28 may be implemented for example using an Acuson 128 XP system or an Acuson Sequoia system, both of which are readily available.

The transmit/receive system 28 supplies Doppler information to frame memories 30. In the following example, the Doppler information takes the form of Doppler velocity measurements at respective points in the respective image planes 24, 26. It will be recognized that the techniques described below can be adapted for use with other Doppler parameters such as Doppler energy, power or the like.

Doppler parameters stored as images in the frame memories 30 can be supplied to a display system 34 for display. Alternately, the Doppler parameters of the frame memories 30 can be further processed by a velocity processor 32 for display by the display system 34. The velocity processor 32 receives additional input signals from a device 36 which allows a user to mark a region of interest (ROI), and by a device 38 which supplies an input signal related to the electrocardiograph of the subject.

Figure 2:
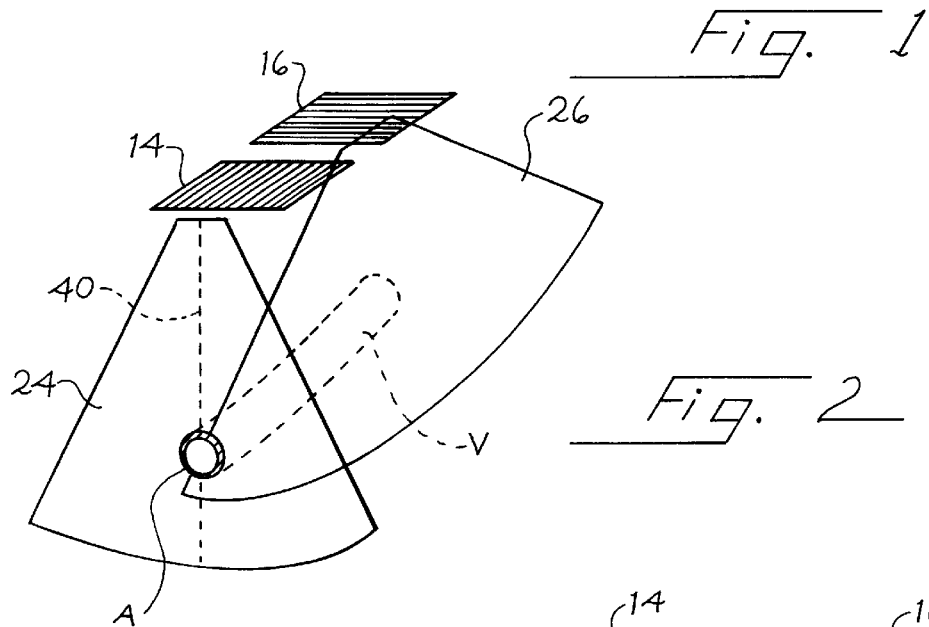
FIG. 2 is a schematic perspective view showing the central image planes of the two transducer arrays of FIG. 1.

FIG. 2 shows a schematic perspective view of the central image planes 24, 26 described above, during imaging of a vessel V. As shown in FIG. 2 the image planes 24, 26 are perpendicular to one another. In this embodiment the image plane 24 is oriented substantially perpendicularly to the longitudinal axis of the vessel V. The reference symbol A is used to designate the area of the vessel V in the image plane 24. Note that the vessel V is imaged with the centerline of the vessel V lying on the centerline 40 of the image plane 24. Since the image plane 26 intersects the image plane 24 along the centerline 40, this ensures that the cross-sectional area A is imaged in the image plane 24, and that a line of the area A is imaged in the image plane 26.

Figure 3:
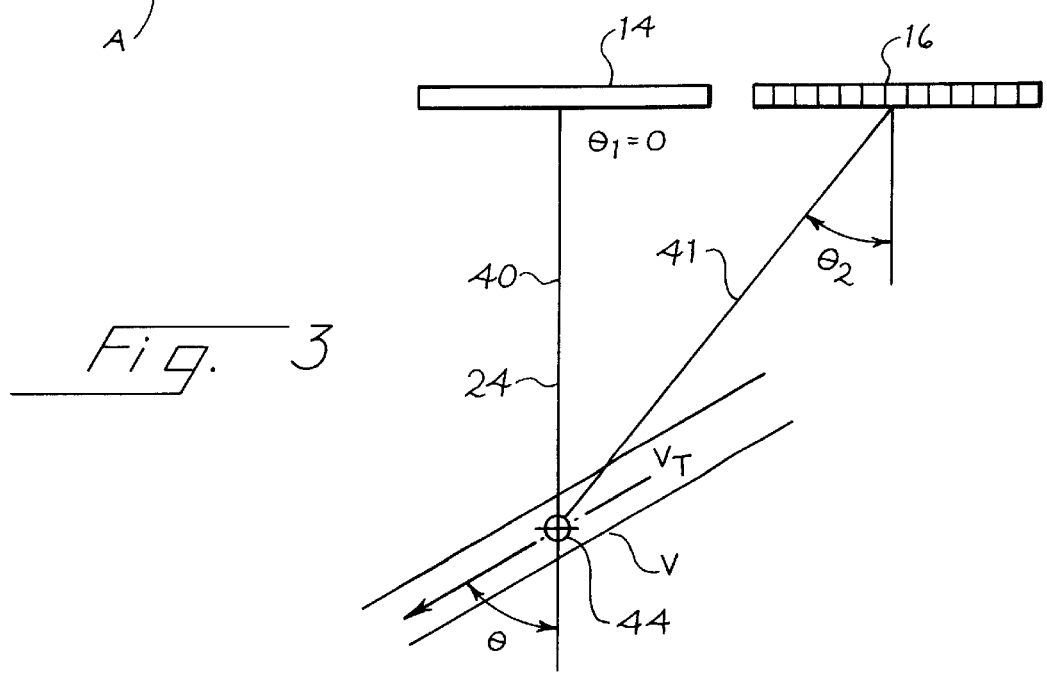
FIG. 3 is a schematic view of the transducer arrays of FIG. 2, taken in the central image plane of the second transducer array.

FIG. 3 is a schematic view taken in the image plane 26 showing the relevant geometry. In FIG. 3 the central image plane 24 of the first transducer array 14 is perpendicular to the plane of the drawing. The reference numeral 44 is used to designate the central point in the vessel V on the centerline 40, and the symbol VT is used to designate the flow vector of blood in the vessel V flowing through the point 44.

In FIG. 3 the symbol $\theta$ is used to designate the Doppler angle, the angle between the centerline 40 and the velocity VT. $\theta_1$ is the angle between the centerline 40 and the perpendicular to the first transducer array 14. ($\theta_1$ is equal to zero in this embodiment, though $\theta_1$ may take non-zero values if desired.) $\theta_2$ is equal to the angle between (1) the scan line 41 passing between the point 44 and the center of the transducer array 16, and (2) the line normal to the transducer array 16. In general, $\theta_2$ will be in the range of 0°–90°, and preferably in the range of 5°–45°. As explained above, the transmit/receive system 28 of FIG. 1 processes signals from the first transducer array 14 to measure the apparent Doppler velocity at the point 44, referred to as V1 here. V1 is equal to the component of VT parallel to the centerline 40. That is, V1 equals VT·cos($\theta_1-\theta$). Similarly, the transmit/receive system 28 processes receive signals from the second transducer array 16 to measure a second apparent Doppler velocity (V2) at the point 44. According to the same principles, V2 is equal to VT·cos($\theta_2-\theta$).

FIGS. 4 and 5 show the images on the central image planes 24, 26, respectively, as displayed on the display system 34. Note that the displayed central image plane 24 includes a cross-sectional view of the vessel V. The vessel V in this view is surrounded by a region of interest (ROI) box 42 which designates the region for which color Doppler is to be displayed. The center of the ROI box 42 is shown by a cursor symbol 45, which is superimposed on the point 44 of FIG. 3.

The central image plane 26 of the second transducer array 16 displays a longitudinal section of the vessel V (FIG. 5).

Reference symbol 46 is used to designate the point 44 of FIG. 3. Since point 44 is on the centerline 40 (FIG. 2), and the image plane 26 intersects the image plane 24 at the centerline 40, the point 44 will appear in the longitudinal section of FIG. 5. FIGS. 4 and 5 represent contents of the frame memories 30. The user positions the ROI box 42 on the cross-sectional view (FIG. 4). The cursor symbol 45 (eg a small cross) is automatically displayed at the center of the ROI. Since the system knows the geometry of the two arrays 14, 16 and depth of the cursor symbol 45 on the first (cross-sectional) image, it can calculate the corresponding unique point on the longitudinal view (FIG. 5).

As shown in FIG. 6, the velocity processor 32 includes separate sections for generating separate displays. The velocity correction section 50 corrects the apparent Doppler velocities as measured by the first transducer array 14. The velocity display section 52 calculates various velocity metrics based on corrected velocities as described below. The flow rate display section 54 calculates various flow rates based on corrected velocity as described below. The total flow display section 56 calculates the total flow through the vessel V for various time intervals. The following paragraphs will describe the operation of each of the sections 50–56.

The velocity correction section 50 utilizes measures of apparent Doppler velocity V1, V2 at the point 44 as measured in the two image planes 24, 26. Using the known spatial separation between the arrays 14, 16 and the measured depth of the point 44 from the array 14, the velocity correction section 50 calculates the ratio of the apparent velocities V1/V2 for the point 44. Using the calculated ratio to address a two-dimensional look-up table, the corresponding correction factor to be applied to the color velocity information in the image plane 24 is determined. This factor is then applied to the color flow information in the image plane 24 to obtain the true velocity. More simply, the color map can be rescaled to accurately correspond to the true velocity rather than the apparent velocity. Once corrected velocities have been obtained in the cross-sectional image of the plane 24, any one of the metrics described below can readily be obtained.

By way of example, to illustrate the operation of the velocity correction section 50, it will be assumed that each of the arrays 14, 16 measures 10 mm by 10 mm, that the arrays 14, 16 are offset from one another by 11 mm, and that $\theta_1$ is zero. In this example it will be assumed that the vessel V is the carotid artery at a depth of 19 mm from the face of the transducer 14. In this example the angle difference $\theta_2-\theta_1$ is approximately 30°, and the observed velocity ratio V1/V2 between apparent velocity measurements in the planes 24, 26 is 0.74. That is, the apparent velocity for the point 46 in the cross-section view of the plane 24 is 0.74 times the apparent velocity for the point 46 in the longitudinal axis view of plane 26. This relationship is set out in Equation 1 below:

$$\frac{V1}{V2} = \frac{VT\cos(\Theta_1 - \Theta)}{VT\cos(\Theta_2 - \Theta)} = 0.74 \qquad \text{(Equation 1)}$$

In this equation VT is the actual velocity of a blood passing through the point 44 as shown in FIG. 3, V1 is the apparent Doppler velocity at the point 44 measured by the array 14 along the scan line 40, and V2 is the apparent Doppler velocity measured by the array 16 along the scan line 41. $\theta_1$ is the angle of the scan line 40 with respect to the array normal (0° in this example), and $\theta_2$ is the angle of the scan line 41 to the array normal (30° in this example). $\theta$ is the angle of the actual flow VT with respect to the array normal.

There is only one solution to Equation 1 for $\theta_1-\theta$, for practically obtainable values of $\theta_1$, $\theta_2$ and V1/V2. In this example $\theta_1-\theta$ is equal to 44°, and therefore $\theta_2-\theta$ is equal to 14°. Thus, the correction factor to be applied to the apparent velocity V1 is 1/cos 44°=1.39. These correction factors can be kept in a look-up table used by the velocity correction section 50. Interpolation may be used if the exact values for a particular pair of input parameter $\theta_2$ and V1/V2 are not stored in the look-up table.

Table 1 may be used to derive $\theta$ and the corresponding correction factor for a known $\theta_2$ and V1/V2 ratio. It is assumed in the development of this table that $\theta_1=0$, but Table 1 may be recalculated for other values of $\theta_1$ if required, or other ranges of $\theta$ and V1/V2, using Equation 1. Table 1 may be used as follows. For the measured $\theta_2$ (30 degrees in this case), select the relevant column. Go down the column until the observed velocity ratio is found—this on the 22nd row in this case. Go along the row and observe that the required value for $\theta$ to satisfy Equation 1 is 44 degrees. Hence, the correction factor to be applied to VI to obtain VT is 1/cos(44 degrees)=1.39. Notice that if $\theta=90$ degrees, there is no Doppler level measured by the array 14 and hence no correction is obtainable. Additionally, if the value $\theta-\theta_2$ is close 90 degrees, the observed ratio V1/V2 is ill conditioned (tends to very high numbers) and may not produce a useful correction. In practice, these ill-conditioned situations can be avoided by user manipulation of the array. As an example, if the system detects an ill-conditioned case, it can prompt the user to re-scan using a different angle.

Figure 10:
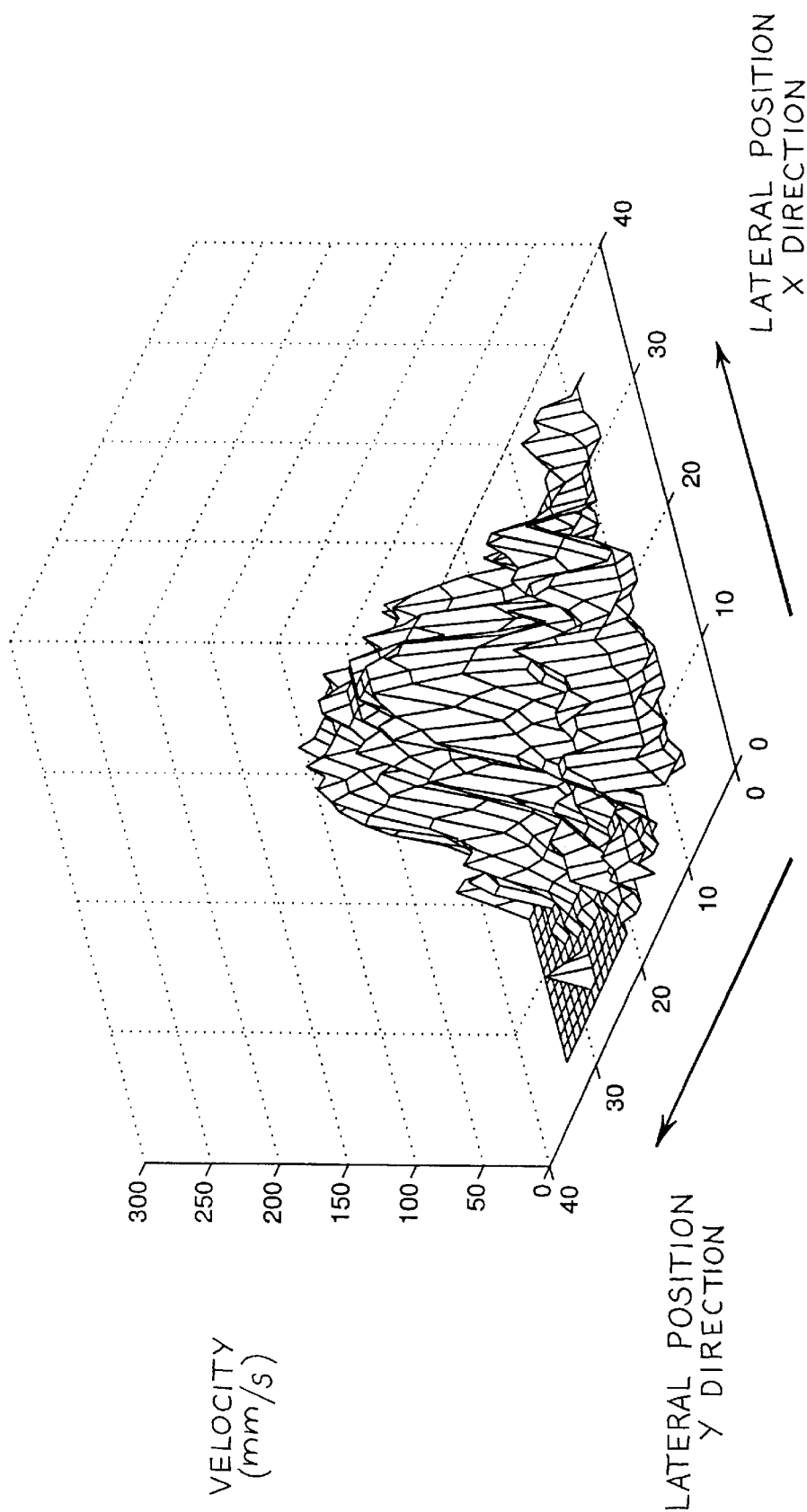
FIG. 10 is a plot of apparent Doppler velocity across the cross-section of a carotid artery.
Figure 11:
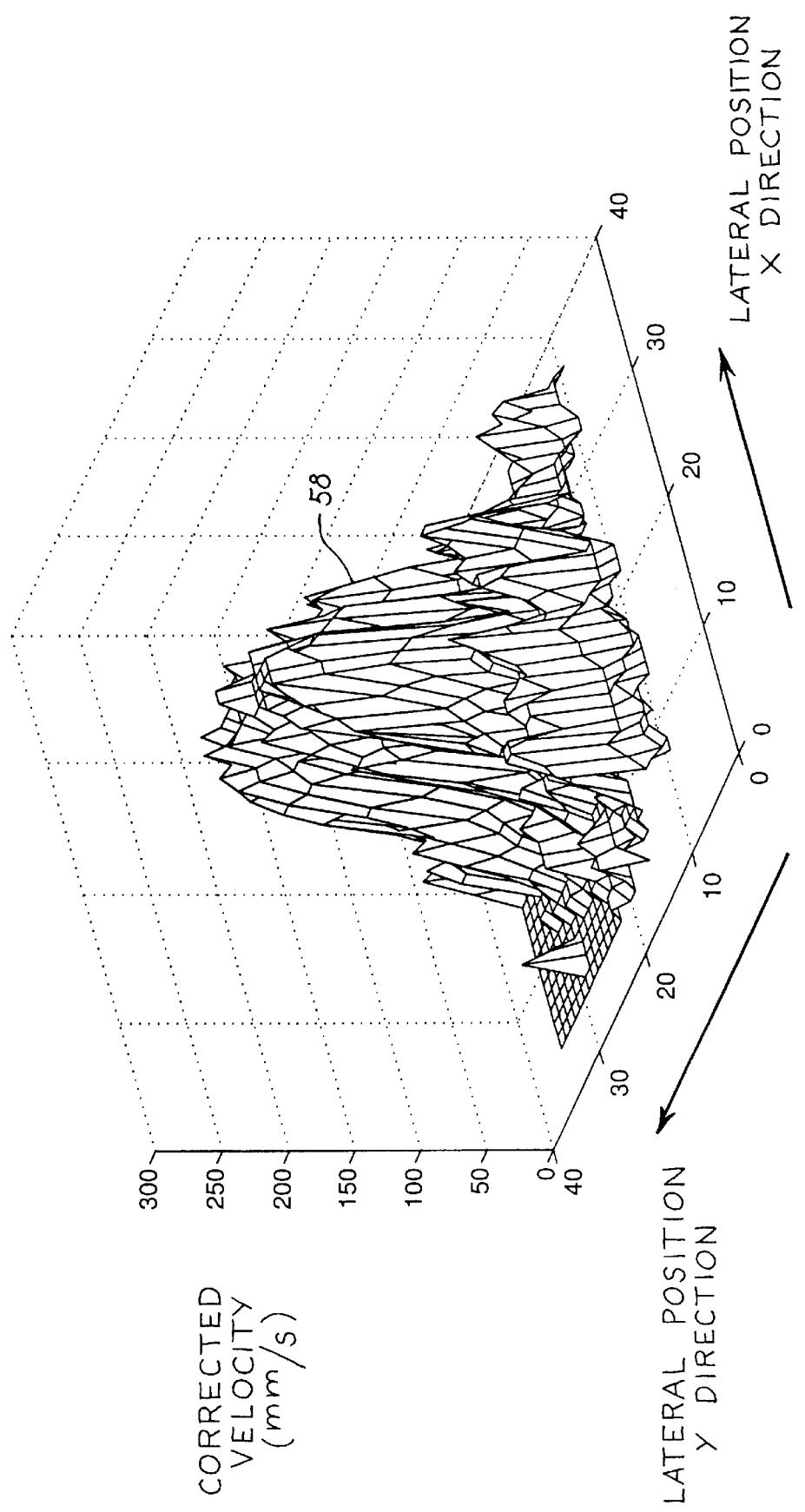
FIG. 11 is a plot of the data of FIG. 10 corrected by a correction factor equal to 1.39 to show actual velocity.

FIGS. 10 and 11 illustrate one suitable output for the velocity correction section 50. FIG. 12 shows the apparent velocity V1 at various points along the cross-sectional area A of the vessel V as measured with the first transducer array 14 in the image plane 24. FIG. 11 shows the same data after the correction factor of 1.39 as derived in the foregoing example has been applied. The actual velocity for the carotid artery can be displayed on the display system 34 by suitably assigning colors to the velocity values shown in FIG. 11 to provide a conventional two-dimensional color flow image, in which the displayed velocity has been corrected as described above to take into account the fact that the apparent velocity V1 measured with the first transducer array 14 is only the velocity component along the scan line of the measurement.

The system may be programmed to display the calculated value of $\theta$ to provide the user with an indication of how well conditioned (numerically) the correction is likely to be. For example, if $\theta$ is near 90°, the correction may not be reliable.

Once the apparent velocities as measured with the array 14 in the cross-section A of FIG. 4 have been corrected by the velocity correction section 14, these corrected velocity measurements can be used to generate a number of metrics. The velocity display section 52 generates any of the velocity metrics shown in the display region 60 of FIG. 7. In each case it is the actual or corrected velocity VT that is used to generate the displayed value, rather than the apparent velocity V1 generated by the transmit/receive system 28.

As shown in FIG. 7, the velocity display section 52 generates the actual velocity at the cursor, simply by selecting the actual velocity VT for the appropriate X, Y location. The velocity display section 52 also displays the peak velocity over the region of interest, as for example the peak actual velocity VT in the area A. The section 52 also calculates the peak velocity over time, that is the peak actual velocity VT over a designated two or three-dimensional region and over a plurality of successive frames taken at respective times. For example, if the times are taken over a complete heart cycle, the peak velocity can represent the peak actual velocity VT observed in the vessel V over a heartbeat cycle.

The section 52 also determines and displays the mean velocity over the region of interest by summing the true velocity VT over the region of interest and dividing by the total number of pixels included in the sum. By using the control signal from the EKG device 38, the section 52 can determine the actual velocity VT at the cursor 45 at a particular time T1 after a benchmark in the EKG such as the R-wave.

The velocity rate display section 54 operates to generate for display any of a number of flow rate parameters, as shown in the display region 62 of FIG. 7. One useful flow rate parameter is the total flow rate over the region of interest. The total flow rate is equal to the sum of all of the actual velocities VT in the area A multiplied by the area of the pixel corresponding to each measurement of velocity VT. Preferably, the flow rate is corrected to take into account that the central image plane 24 is in general not exactly perpendicular to the vessel V. This can be done by multiplying the integrated flow by a constant equal to the absolute value of $\sin(\theta_1-\theta)$. Similarly, the section 54 calculates and displays the peak total flow rate over a heartbeat cycle, which is simply the maximum total flow rate of a plurality of frames that encompass one complete EKG cycle as determined by the EKG input device 38. If desired, the section 54 can calculate and display the mean total flow rate, which is the average total flow rate, calculated as described above, over a determined time period, which can be equal to one or more heartbeat cycles, or a selected number of seconds or minutes.

It will be observed that the velocity correction section 50 applies a correction equal to $1/\cos(\theta_1-\theta)$ and the flow rate display section 54 applies a correction equal to the absolute value of $\sin(\theta_1-\theta)$. If desired, the flow rate display section 54 can operate on the uncorrected velocity data V1, and can apply an equivalent correction equal to the tangent of the absolute value of $(\theta_1-\theta)$.

Finally, in this example the section 54 can determine and display the total flow rate calculated as described above at a selected time T1 after the R wave of the EKG input.

Once the flow rate has been calculated as described above, the total flow display section 56 can display total flow or stroke volume metrics, as shown in the display region 64 of FIG. 7. Stroke volume is determined as an integrated value over one heartbeat cycle of the total flow rate times the differential time between measures of the total flow rate. Similarly, the section 56 measures the mean stroke volume, which is the average of a selected number of stroke volumes, calculated as described above.

Figure 8:
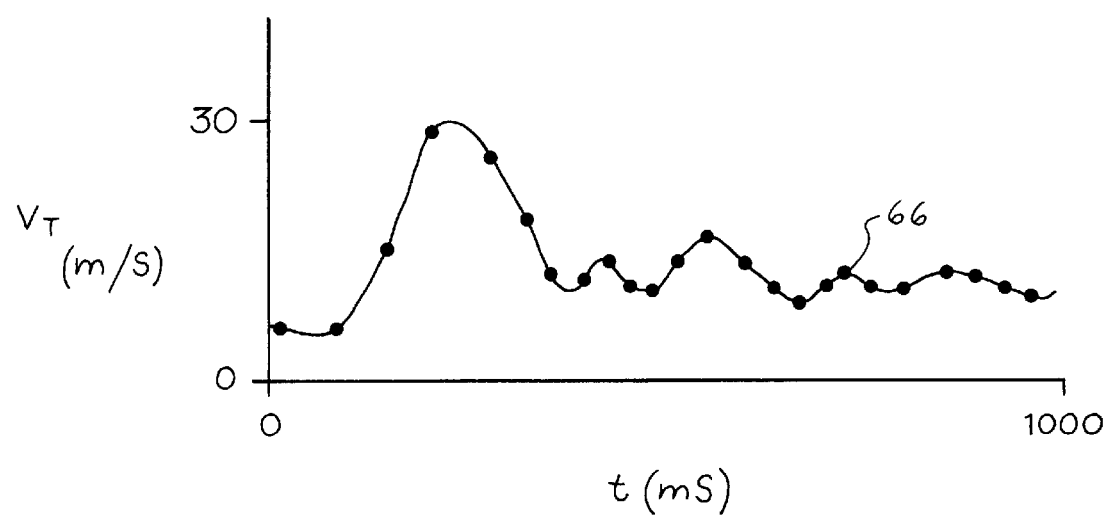
FIGS. 8 and 9 are schematic views of graphs generated by the display processor of FIG. 1.
Figure 9:
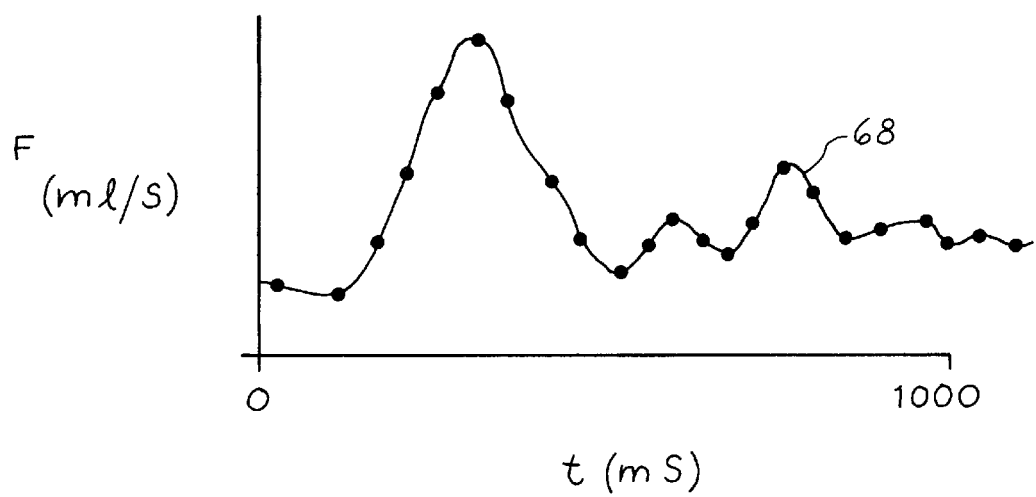

As shown in FIGS. 8 and 9, the velocity display section 52 and the flow rate display section 54 generate graphs showing the time evolution of the velocity VT and the total flow rate F, respectively. The graphs of FIGS. 8 and 9 start at identical points in the heart beat cycle, and they show the fluctuation of actual velocity VT and total flow rate F during the course of the heartbeat cycle.

Preferably, the system 10 of FIG. 1 is arranged to minimize the time difference between the measurement of apparent velocities V1, V2. This can be accomplished for example by programming the system 28 to alternate between color Doppler lines with the array 14 and color Doppler lines with the array 16 so that the time delay between the observation at the point 44 with the two arrays 14, 16 is only the time difference between consecutive lines, and not the time difference between consecutive frames.

As an alternative, it is not required that the two transducer arrays 14, 16 be used independently of one another as described above. For example, signals can be transmitted via the second array 16 and the echoes of these signals received via the first array 14.

The velocity correction used to determine the actual velocity VT provides the highest accuracy when the velocities V1, V2 are from the same physical sample of moving tissue. Because of inevitable refraction and mis-alignment, it may be that the theoretically aligned points 44, 46 of FIGS. 4 and 6 are not exactly physically aligned. In order to overcome this problem the velocity correction section 50 is preferably programmed to search a first small matrix of points around the point 44 and a second small matrix of points around the point 46 in order to determine the highest detected velocity V1 within the search region in the plane 24 and the highest detected velocity V2 within the search region in the plane 26. This can be done in terms of single observations or as a spatial distribution of velocity observations from both arrays which match. By using the highest detected velocities V1, V2 in the respective search regions, any small beam bending due to refraction is compensated. For example, if the maximum value V1 near the point 44 is found at location (X, Y) and the maximum value V2 near the point 46 is found at location (X-Δ, Y-Δ) then it is the maximum value V1 at (X, Y) and the maximum value V2 at (X-Δ, Y-Δ) that are used in Equation 1 above.

Note that if the velocity profile is relatively flat over the region closely adjacent to the point 44, and hence there is ambiguity about where the maximum V1 actually is, that does not degrade the accuracy of the correction. It is only the ratio of the maximum values V1, V2 that is significant in this application.

The velocity processor can be implemented most simply as a series of software routines executed by the system computer. Alternately, dedicated digital hardware summers of pixel velocity values may be used, followed by a multiplication by the desired correction factor. The calculations performed by the velocity processor may be repeated at approximately the frame rate of the color Doppler signals, such as 20 frames per second.

If there is back flow detected at any time in the cycle, such back flow is detected as a negative value of flow and is subtracted in the calculation of total flow rate. Optionally, the system 10 can be programmed to provide a visual prompt or warning (such as a flashing icon or a message) if negative flow is detected under certain circumstances.

Optionally, the electrocardiogram signal can be monitored, and if one cycle does not closely match a previous cycle (for example the R signal is weak due to electrical contact problems, electrical corrupting noise, or an erratic heartbeat), then the corresponding flow calculation for the cycle can be abandoned.

Of course, it should be recognized that a wide range of changes and modifications can be made to the preferred embodiments described above. As pointed out above, this invention can be adapted to other Doppler parameters than velocity, such as for example Doppler power. Furthermore, this invention is not restricted to use with two dimensional Doppler images, but can readily be adapted for use with three dimensionally organized data. The 3D case may be most simply considered as a sequence of largely parallel, but finely spaced, cross-sectional views—each with corresponding perpendicular observations being made so as to provide corresponding correcting factors. Once all these 2D planes have been corrected, the corrected 2D Doppler information may be combined using spatial locating information relating to the individual planes to obtain a desired 3D observation of corrected velocity flow. Reconstruction and display techniques for going from multiple 2D planes to 3D volumes are well known in the art.

It is therefore intended that the foregoing detailed description be regarded as an illustration of several preferred forms of the invention, and not as a limitation. It is only the following claims, including all equivalents, which are intended to define the scope of this invention.

TABLE 1

| $\theta_2$ | | | | | | | | | | | | | |
|---|---|---|---|---|---|---|---|---|---|---|---|---|---|
| 2.50 | 5.00 | 7.50 | 10.00 | 12.50 | 15.00 | 17.50 | 20.00 | 22.50 | 25.00 | 27.50 | 30.00 | 32.50 | 35.00 |
| 1.00 | 1.00 | 1.00 | 1.01 | 1.02 | 1.03 | 1.04 | 1.05 | 1.07 | 1.09 | 1.11 | 1.13 | 1.16 | 1.19 |
| 1.00 | 1.00 | 1.00 | 1.00 | 1.01 | 1.02 | 1.03 | 1.04 | 1.05 | 1.07 | 1.09 | 1.11 | 1.14 | 1.16 |
| 1.00 | 0.99 | 0.99 | 1.00 | 1.00 | 1.01 | 1.01 | 1.02 | 1.04 | 1.05 | 1.07 | 1.09 | 1.11 | 1.14 |
| 0.99 | 0.99 | 0.99 | 0.99 | 0.99 | 1.00 | 1.00 | 1.01 | 1.02 | 1.04 | 1.05 | 1.07 | 1.09 | 1.11 |
| 0.99 | 0.99 | 0.99 | 0.98 | 0.99 | 0.99 | 0.99 | 1.00 | 1.01 | 1.02 | 1.03 | 1.05 | 1.07 | 1.09 |
| 0.99 | 0.99 | 0.98 | 0.98 | 0.98 | 0.98 | 0.98 | 0.99 | 0.99 | 1.00 | 1.02 | 1.03 | 1.04 | 1.06 |
| 0.99 | 0.98 | 0.98 | 0.97 | 0.97 | 0.97 | 0.97 | 0.98 | 0.98 | 0.99 | 1.00 | 1.01 | 1.02 | 1.04 |
| 0.99 | 0.98 | 0.97 | 0.97 | 0.96 | 0.96 | 0.96 | 0.96 | 0.97 | 0.97 | 0.98 | 0.99 | 1.00 | 1.02 |
| 0.99 | 0.98 | 0.97 | 0.96 | 0.96 | 0.95 | 0.95 | 0.95 | 0.95 | 0.96 | 0.96 | 0.97 | 0.98 | 0.99 |
| 0.99 | 0.97 | 0.96 | 0.95 | 0.95 | 0.94 | 0.94 | 0.94 | 0.94 | 0.94 | 0.95 | 0.95 | 0.96 | 0.97 |
| 0.98 | 0.97 | 0.96 | 0.95 | 0.94 | 0.93 | 0.93 | 0.93 | 0.93 | 0.93 | 0.93 | 0.94 | 0.94 | 0.95 |
| 0.98 | 0.97 | 0.95 | 0.94 | 0.93 | 0.92 | 0.92 | 0.92 | 0.91 | 0.91 | 0.92 | 0.92 | 0.92 | 0.93 |
| 0.98 | 0.96 | 0.95 | 0.94 | 0.92 | 0.92 | 0.91 | 0.90 | 0.90 | 0.90 | 0.90 | 0.90 | 0.90 | 0.91 |
| 0.98 | 0.96 | 0.94 | 0.93 | 0.92 | 0.91 | 0.90 | 0.89 | 0.89 | 0.88 | 0.88 | 0.88 | 0.89 | 0.89 |
| 0.98 | 0.96 | 0.94 | 0.92 | 0.91 | 0.90 | 0.89 | 0.88 | 0.87 | 0.87 | 0.87 | 0.87 | 0.87 | 0.87 |
| 0.97 | 0.95 | 0.93 | 0.91 | 0.90 | 0.89 | 0.88 | 0.87 | 0.86 | 0.85 | 0.85 | 0.85 | 0.85 | 0.85 |
| 0.97 | 0.95 | 0.93 | 0.91 | 0.89 | 0.88 | 0.86 | 0.85 | 0.85 | 0.84 | 0.83 | 0.83 | 0.83 | 0.83 |
| 0.97 | 0.94 | 0.92 | 0.90 | 0.88 | 0.87 | 0.85 | 0.84 | 0.83 | 0.82 | 0.82 | 0.81 | 0.81 | 0.81 |
| 0.97 | 0.94 | 0.91 | 0.89 | 0.87 | 0.86 | 0.84 | 0.83 | 0.82 | 0.81 | 0.80 | 0.80 | 0.79 | 0.79 |
| 0.97 | 0.94 | 0.91 | 0.88 | 0.86 | 0.85 | 0.83 | 0.82 | 0.80 | 0.79 | 0.78 | 0.78 | 0.77 | 0.77 |
| 0.96 | 0.93 | 0.90 | 0.88 | 0.85 | 0.83 | 0.82 | 0.80 | 0.79 | 0.78 | 0.77 | 0.76 | 0.75 | 0.75 |
| 0.96 | 0.93 | 0.89 | 0.87 | 0.84 | 0.82 | 0.80 | 0.79 | 0.77 | 0.76 | 0.75 | 0.74 | 0.73 | 0.73 |
| 0.96 | 0.92 | 0.89 | 0.86 | 0.83 | 0.81 | 0.79 | 0.77 | 0.76 | 0.74 | 0.73 | 0.72 | 0.71 | 0.71 |
| 0.95 | 0.91 | 0.88 | 0.85 | 0.82 | 0.80 | 0.78 | 0.76 | 0.74 | 0.73 | 0.71 | 0.70 | 0.69 | 0.69 |
| 0.95 | 0.91 | 0.87 | 0.84 | 0.81 | 0.78 | 0.76 | 0.74 | 0.72 | 0.71 | 0.70 | 0.68 | 0.67 | 0.67 |
| 0.95 | 0.90 | 0.86 | 0.83 | 0.80 | 0.77 | 0.75 | 0.73 | 0.71 | 0.69 | 0.68 | 0.66 | 0.65 | 0.64 |
| 0.94 | 0.90 | 0.85 | 0.82 | 0.78 | 0.76 | 0.73 | 0.71 | 0.69 | 0.67 | 0.66 | 0.64 | 0.63 | 0.62 |
| 0.94 | 0.89 | 0.84 | 0.80 | 0.77 | 0.74 | 0.71 | 0.69 | 0.67 | 0.65 | 0.64 | 0.62 | 0.61 | 0.60 |
| 0.94 | 0.88 | 0.83 | 0.79 | 0.76 | 0.72 | 0.70 | 0.67 | 0.65 | 0.63 | 0.62 | 0.60 | 0.59 | 0.58 |
| 0.93 | 0.87 | 0.82 | 0.78 | 0.74 | 0.71 | 0.68 | 0.65 | 0.63 | 0.61 | 0.59 | 0.58 | 0.56 | 0.55 |
| 0.92 | 0.86 | 0.81 | 0.76 | 0.72 | 0.69 | 0.66 | 0.63 | 0.61 | 0.59 | 0.57 | 0.55 | 0.54 | 0.53 |
| 0.92 | 0.85 | 0.79 | 0.75 | 0.70 | 0.67 | 0.64 | 0.61 | 0.59 | 0.56 | 0.55 | 0.53 | 0.51 | 0.50 |
| 0.91 | 0.84 | 0.78 | 0.73 | 0.68 | 0.65 | 0.61 | 0.59 | 0.56 | 0.54 | 0.52 | 0.50 | 0.49 | 0.47 |

TABLE 1-continued

| | | | | | | | | | | | | | |
|---|---|---|---|---|---|---|---|---|---|---|---|---|---|
| 0.90 | 0.83 | 0.76 | 0.71 | 0.66 | 0.62 | 0.59 | 0.56 | 0.53 | 0.51 | 0.49 | 0.48 | 0.46 | 0.45 |
| 0.89 | 0.81 | 0.74 | 0.68 | 0.64 | 0.60 | 0.56 | 0.53 | 0.51 | 0.48 | 0.46 | 0.45 | 0.43 | 0.42 |
| 0.88 | 0.79 | 0.72 | 0.66 | 0.61 | 0.57 | 0.53 | 0.50 | 0.48 | 0.45 | 0.43 | 0.42 | 0.40 | 0.39 |
| 0.87 | 0.77 | 0.69 | 0.63 | 0.58 | 0.54 | 0.50 | 0.47 | 0.44 | 0.42 | 0.40 | 0.38 | 0.37 | 0.35 |
| 0.85 | 0.74 | 0.66 | 0.59 | 0.54 | 0.50 | 0.46 | 0.43 | 0.41 | 0.38 | 0.37 | 0.35 | 0.33 | 0.32 |
| 0.83 | 0.71 | 0.62 | 0.56 | 0.50 | 0.46 | 0.42 | 0.39 | 0.37 | 0.35 | 0.33 | 0.31 | 0.30 | 0.28 |
| 0.80 | 0.67 | 0.58 | 0.51 | 0.45 | 0.41 | 0.38 | 0.35 | 0.32 | 0.30 | 0.29 | 0.27 | 0.26 | 0.25 |
| 0.76 | 0.62 | 0.52 | 0.45 | 0.40 | 0.36 | 0.32 | 0.30 | 0.27 | 0.26 | 0.24 | 0.23 | 0.21 | 0.20 |
| 0.71 | 0.55 | 0.45 | 0.38 | 0.33 | 0.29 | 0.26 | 0.24 | 0.22 | 0.20 | 0.19 | 0.18 | 0.17 | 0.16 |
| 0.62 | 0.45 | 0.35 | 0.29 | 0.25 | 0.21 | 0.19 | 0.17 | 0.16 | 0.14 | 0.13 | 0.12 | 0.12 | 0.11 |
| 0.44 | 0.29 | 0.21 | 0.17 | 0.14 | 0.12 | 0.10 | 0.09 | 0.08 | 0.08 | 0.07 | 0.07 | 0.06 | 0.06 |
| 0.00 | 0.00 | 0.00 | 0.00 | 0.00 | 0.00 | 0.00 | 0.00 | 0.00 | 0.00 | 0.00 | 0.00 | 0.00 | 0.00 |
| −4.00 | −0.67 | −0.36 | −0.25 | −0.19 | −0.16 | −0.13 | −0.11 | −0.10 | −0.09 | −0.08 | −0.07 | −0.07 | −0.06 |
| 2.66 | −4.00 | −1.14 | −0.67 | −0.47 | −0.37 | −0.30 | −0.25 | −0.22 | −0.19 | −0.17 | −0.16 | −0.15 | −0.14 |
| 1.71 | 5.99 | −3.99 | −1.50 | −0.92 | −0.67 | −0.52 | −0.43 | −0.37 | −0.32 | −0.29 | −0.26 | −0.23 | −0.22 |
| 1.45 | 2.66 | undf | −3.99 | −1.77 | −1.14 | −0.84 | −0.67 | −0.56 | −0.48 | −0.42 | −0.37 | −0.34 | −0.31 |
| 1.33 | 1.99 | 3.98 | undf | −3.98 | −1.99 | −1.33 | −1.00 | −0.80 | −0.67 | −0.58 | −0.51 | −0.45 | −0.41 |
| 1.26 | 1.71 | 2.65 | 5.96 | undf | −3.97 | −2.17 | −1.49 | −1.14 | −0.92 | −0.78 | −0.67 | −0.59 | −0.53 |
| 1.21 | 1.55 | 2.14 | 3.47 | 9.24 | undf | −3.96 | −2.31 | −1.64 | −1.27 | −1.04 | −0.88 | −0.76 | −0.68 |
| 1.18 | 1.44 | 1.86 | 2.64 | 4.52 | undf | undf | −3.95 | '2.43 | −1.76 | −1.38 | −1.14 | −0.97 | −0.85 |
| 1.16 | 1.37 | 1.70 | 2.22 | 3.22 | 5.90 | undf | −8.85 | −3.94 | −2.54 | −1.87 | −1.49 | −1.23 | −1.06 |
| 1.14 | 1.32 | 1.58 | 1.97 | 2.62 | 3.92 | 7.84 | undf | −7.84 | −3.92 | −2.62 | −1.97 | −1.58 | −1.32 |
| 1.12 | 1.28 | 1.40 | 1.80 | 2.27 | 3.07 | 4.77 | undf | undf | −7.16 | −3.91 | −2.69 | −2.06 | −1.67 |
| 1.11 | 1.25 | 1.43 | 1.68 | 2.04 | 2.60 | 3.59 | 5.83 | undf | undf | −6.66 | −3.89 | −2.75 | −2.13 |
| 1.10 | 1.22 | 1.38 | 1.59 | 1.88 | 2.30 | 2.97 | 4.19 | 7.18 | undf | undf | −6.28 | −3.87 | −2.80 |
| 1.09 | 1.20 | 1.34 | 1.52 | 1.76 | 2.09 | 2.58 | 3.37 | 4.90 | 8.97 | undf | undf | −5.98 | −3.85 |
| 1.08 | 1.18 | 1.31 | 1.46 | 1.66 | 1.93 | 2.31 | 2.88 | 3.83 | 5.74 | undf | undf | undf | −5.74 |
| 1.08 | 1.17 | 1.28 | 1.41 | 1.59 | 1.81 | 2.12 | 2.55 | 3.21 | 4.35 | 6.75 | undf | undf | undf |
| 1.07 | 1.15 | 1.25 | 1.37 | 1.53 | 1.72 | 1.97 | 2.31 | 2.80 | 3.57 | 4.94 | 8.02 | undf | undf |
| 1.06 | 1.14 | 1.23 | 1.34 | 1.47 | 1.64 | 1.85 | 2.13 | 2.52 | 3.08 | 3.98 | 5.62 | 9.63 | undf |
| 1.06 | 1.13 | 1.21 | 1.31 | 1.43 | 1.58 | 1.76 | 1.99 | 2.30 | 2.74 | 3.38 | 4.42 | 6.42 | undf |
| 1.06 | 1.12 | 1.20 | 1.29 | 1.39 | 1.52 | 1.68 | 1.88 | 2.14 | 2.40 | 2.97 | 3.70 | 4.92 | 7.38 |
| 1.05 | 1.11 | 1.18 | 1.26 | 1.36 | 1.47 | 1.61 | 1.79 | 2.00 | 2.29 | 2.67 | 3.22 | 4.05 | 5.49 |
| 1.05 | 1.10 | 1.17 | 1.24 | 1.33 | 1.43 | 1.56 | 1.71 | 1.90 | 2.13 | 2.45 | 2.87 | 3.48 | 4.44 |
| 1.05 | 1.10 | 1.16 | 1.22 | 1.30 | 1.40 | 1.51 | 1.64 | 1.80 | 2.01 | 2.27 | 2.61 | 3.08 | 3.77 |
| 1.04 | 1.09 | 1.14 | 1.21 | 1.28 | 1.36 | 1.46 | 1.58 | 1.73 | 1.90 | 2.12 | 2.40 | 2.78 | 3.30 |
| 1.04 | 1.08 | 1.13 | 1.19 | 1.26 | 1.34 | 1.43 | 1.53 | 1.66 | 1.81 | 2.00 | 2.24 | 2.55 | 2.96 |
| 1.04 | 1.08 | 1.12 | 1.18 | 1.24 | 1.31 | 1.39 | 1.49 | 1.60 | 1.74 | 1.90 | 2.10 | 2.36 | 2.70 |
| 1.03 | 1.07 | 1.12 | 1.16 | 1.22 | 1.29 | 1.36 | 1.45 | 1.55 | 1.67 | 1.81 | 1.99 | 2.21 | 2.48 |
| 1.03 | 1.07 | 1.11 | 1.15 | 1.20 | 1.26 | 1.33 | 1.41 | 1.50 | 1.61 | 1.74 | 1.89 | 2.08 | 2.31 |
| 1.03 | 1.06 | 1.10 | 1.14 | 1.19 | 1.24 | 1.31 | 1.38 | 1.46 | 1.56 | 1.67 | 1.81 | 1.97 | 2.17 |
| 1.03 | 1.06 | 1.09 | 1.13 | 1.17 | 1.22 | 1.28 | 1.35 | 1.42 | 1.51 | 1.61 | 1.73 | 1.88 | 2.05 |
| 1.02 | 1.05 | 1.08 | 1.12 | 1.16 | 1.21 | 1.26 | 1.32 | 1.39 | 1.47 | 1.56 | 1.67 | 1.79 | 1.94 |
| 1.02 | 1.05 | 1.08 | 1.11 | 1.15 | 1.19 | 1.24 | 1.29 | 1.36 | 1.43 | 1.51 | 1.61 | 1.72 | 1.85 |
| 1.02 | 1.04 | 1.07 | 1.10 | 1.14 | 1.18 | 1.22 | 1.27 | 1.33 | 1.39 | 1.47 | 1.55 | 1.66 | 1.77 |
| 1.02 | 1.04 | 1.07 | 1.09 | 1.13 | 1.16 | 1.20 | 1.25 | 1.30 | 1.36 | 1.43 | 1.51 | 1.60 | 1.70 |
| 1.02 | 1.04 | 1.06 | 1.09 | 1.11 | 1.15 | 1.18 | 1.23 | 1.27 | 1.33 | 1.39 | 1.46 | 1.54 | 1.64 |
| 1.02 | 1.03 | 1.05 | 1.08 | 1.10 | 1.13 | 1.17 | 1.21 | 1.25 | 1.30 | 1.36 | 1.42 | 1.50 | 1.58 |
| 1.01 | 1.03 | 1.05 | 1.07 | 1.09 | 1.12 | 1.15 | 1.19 | 1.23 | 1.27 | 1.33 | 1.38 | 1.45 | 1.53 |
| 1.01 | 1.03 | 1.04 | 1.06 | 1.08 | 1.11 | 1.14 | 1.17 | 1.21 | 1.25 | 1.30 | 1.35 | 1.41 | 1.48 |
| 1.01 | 1.02 | 1.04 | 1.05 | 1.07 | 1.10 | 1.12 | 1.15 | 1.19 | 1.22 | 1.27 | 1.32 | 1.37 | 1.43 |
| 1.01 | 1.02 | 1.03 | 1.05 | 2.0 | 1.09 | 1.11 | 1.141 | 1.17 | 1.20 | 1.24 | 1.29 | 1.34 | 1.39 |
| 1.01 | 1.02 | 1.03 | 1.04 | 1.06 | 1.08 | 1.10 | 1.12 | 1.15 | 1.18 | 1.22 | 1.26 | 1.30 | 1.35 |
| 1.01 | 1.01 | 1.02 | 1.03 | 1.05 | 1.07 | 1.08 | 1.11 | 1.13 | 1.16 | 1.19 | 1.23 | 1.27 | 1.32 |
| 1.00 | 1.01 | 1.02 | 1.03 | 1.04 | 1.06 | 1.07 | 1.09 | 1.11 | 1.14 | 1.17 | 1.20 | 1.24 | 1.28 |
| 1.00 | 1.01 | 1.01 | 1.02 | 1.03 | 1.05 | 1.06 | 1.08 | 1.10 | 1.12 | 1.15 | 1.18 | 1.21 | 1.25 |

| $\theta_2$ | | | | | | Correction | |
|---|---|---|---|---|---|---|---|
| 37.50 | 40.00 | 42.50 | 45.00 | 47.50 | 50.00 | $\theta$ | Factor |
| 1.23 | 1.27 | 1.31 | 1.37 | 1.43 | 1.49 | 2.000 | 1.001 |
| 1.20 | 1.23 | 1.27 | 1.32 | 1.38 | 1.44 | 4.000 | 1.002 |
| 1.17 | 1.20 | 1.24 | 1.28 | 1.33 | 1.38 | 6.000 | 1.006 |
| 1.14 | 1.17 | 1.20 | 1.24 | 1.28 | 1.33 | 8.000 | 1.010 |
| 1.11 | 1.14 | 1.17 | 1.20 | 1.24 | 1.29 | 10.000 | 1.015 |
| 1.08 | 1.11 | 1.14 | 1.17 | 1.20 | 1.24 | 12.000 | 1.022 |
| 1.06 | 1.08 | 1.10 | 1.13 | 1.16 | 1.20 | 14.000 | 1.031 |
| 1.03 | 1.05 | 1.07 | 1.10 | 1.13 | 1.16 | 16.000 | 1.040 |
| 1.01 | 1.03 | 1.05 | 1.07 | 1.09 | 1.12 | 18.000 | 1.051 |
| 0.99 | 1.00 | 1.02 | 1.04 | 1.06 | 1.09 | 20.000 | 1.064 |
| 0.96 | 0.97 | 0.99 | 1.01 | 1.03 | 1.05 | 22.000 | 1.079 |
| 0.94 | 0.95 | 0.96 | 0.98 | 1.00 | 1.02 | 24.000 | 1.095 |
| 0.92 | 0.93 | 0.94 | 0.95 | 0.97 | 0.98 | 26.000 | 1.113 |
| 0.90 | 0.90 | 0.91 | 0.92 | 0.94 | 0.95 | 28.000 | 1.133 |
| 0.87 | 0.88 | 0.89 | 0.90 | 0.91 | 0.92 | 30.000 | 1.155 |
| 0.85 | 0.86 | 0.86 | 0.87 | 0.88 | 0.89 | 32.000 | 1.179 |
| 0.83 | 0.83 | 0.84 | 0.84 | 0.85 | 0.86 | 34.000 | 1.206 |
| 0.81 | 0.81 | 0.81 | 0.82 | 0.83 | 0.83 | 36.000 | 1.236 |

TABLE 1-continued

| | | | | | | | |
|---|---|---|---|---|---|---|---|
| 0.79 | 0.79 | 0.79 | 0.79 | 0.80 | 0.81 | 38.000 | 1.269 |
| 0.77 | 0.77 | 0.77 | 0.77 | 0.77 | 0.78 | 40.000 | 1.305 |
| 0.75 | 0.74 | 0.74 | 0.74 | 0.75 | 0.75 | 42.000 | 1.346 |
| 0.72 | 0.72 | 0.72 | 0.72 | 0.72 | 0.72 | 44.000 | 1.390 |
| 0.70 | 0.70 | 0.70 | 0.69 | 0.69 | 0.70 | 46.000 | 1.440 |
| 0.68 | 0.68 | 0.67 | 0.67 | 0.67 | 0.67 | 48.000 | 1.494 |
| 0.66 | 0.65 | 0.65 | 0.65 | 0.64 | 0.64 | 50.000 | 1.556 |
| 0.64 | 0.63 | 0.62 | 0.62 | 0.62 | 0.62 | 52.000 | 1.624 |
| 0.61 | 0.61 | 0.60 | 0.60 | 0.59 | 0.59 | 54.000 | 1.701 |
| 0.59 | 0.58 | 0.58 | 0.57 | 0.57 | 0.56 | 56.000 | 1.788 |
| 0.57 | 0.56 | 0.55 | 0.54 | 0.54 | 0.54 | 58.000 | 1.887 |
| 0.54 | 0.53 | 0.52 | 0.52 | 0.51 | 0.51 | 60.000 | 2.000 |
| 0.52 | 0.51 | 0.50 | 0.49 | 0.48 | 0.48 | 62.000 | 2.130 |
| 0.49 | 0.48 | 0.47 | 0.46 | 0.46 | 0.45 | 64.000 | 2.281 |
| 0.46 | 0.45 | 0.44 | 0.44 | 0.43 | 0.42 | 66.000 | 2.459 |
| 0.43 | 0.42 | 0.42 | 0.41 | 0.40 | 0.39 | 68.000 | 2.669 |
| 0.41 | 0.39 | 0.39 | 0.38 | 0.37 | 0.36 | 70.000 | 2.924 |
| 0.37 | 0.36 | 0.36 | 0.35 | 0.34 | 0.33 | 72.000 | 3.236 |
| 0.34 | 0.33 | 0.32 | 0.32 | 0.31 | 0.30 | 74.000 | 3.628 |
| 0.31 | 0.30 | 0.29 | 0.28 | 0.28 | 0.27 | 76.000 | 4.134 |
| 0.27 | 0.26 | 0.26 | 0.25 | 0.24 | 0.24 | 78.000 | 4.810 |
| 0.24 | 0.23 | 0.22 | 0.21 | 0.21 | 0.20 | 80.000 | 5.759 |
| 0.20 | 0.19 | 0.18 | 0.17 | 0.17 | 0.16 | 72.000 | 7.185 |
| 0.15 | 0.15 | 0.14 | 0.13 | 0.13 | 0.13 | 84.000 | 9.567 |
| 0.11 | 0.10 | 0.10 | 0.09 | 0.09 | 0.09 | 86.000 | 14.336 |
| 0.05 | 0.05 | 0.05 | 0.05 | 0.05 | 0.04 | 88.000 | 28.654 |
| 0.00 | 0.00 | 0.00 | 0.00 | 0.00 | 0.00 | 90.000 | undf |
| −0.06 | −0.06 | −0.05 | −0.05 | −0.05 | −0.05 | 92.000 | −28.654 |
| −0.13 | −0.12 | −0.11 | −0.11 | −0.10 | −0.10 | 94.000 | −14.336 |
| −0.20 | −0.19 | −0.18 | −0.17 | −0.16 | −0.15 | 96.000 | −9.567 |
| −0.28 | −0.26 | −0.25 | −0.23 | −0.22 | −0.21 | 98.000 | −7.185 |
| −0.38 | −0.35 | −0.32 | −0.30 | −0.29 | −0.27 | 100.000 | −5.759 |
| −0.48 | −0.44 | −0.41 | −0.38 | −0.36 | −0.34 | 102.000 | −4.810 |
| −0.61 | −0.55 | −0.51 | −0.47 | −0.44 | −0.41 | 104.000 | −4.134 |
| −0.75 | −0.68 | −0.62 | −0.57 | −0.53 | −0.49 | 106.000 | −3.628 |
| −0.93 | −0.82 | −0.75 | −0.68 | −0.63 | −0.58 | 108.000 | −3.236 |
| −1.14 | −1.00 | −0.89 | −0.81 | −0.74 | −0.68 | 110.000 | −2.924 |
| −1.40 | −1.12 | −1.07 | −0.96 | −0.87 | −0.80 | 112.000 | −2.669 |
| −1.74 | −1.48 | −1.28 | −1.13 | −1.02 | −0.93 | 114.000 | −2.459 |
| −2.20 | −1.81 | −1.54 | −1.35 | −1.20 | −1.08 | 116.000 | −2.281 |
| −2.84 | −2.26 | −1.88 | −1.61 | −1.41 | −1.25 | 118.000 | −2.130 |
| −3.83 | −2.88 | −2.31 | −1.93 | −1.66 | −1.46 | 120.000 | −2.000 |
| −5.53 | −3.81 | −2.91 | −2.36 | −1.98 | −1.71 | 122.000 | −1.887 |
| −9.16 | −5.35 | −3.78 | −2.93 | −2.40 | −2.03 | 124.000 | −1.788 |
| undf | −8.43 | −5.19 | −3.76 | −2.95 | −2.43 | 126.000 | −1.701 |
| undf | undf | −7.85 | −5.05 | −3.73 | −2.96 | 128.000 | −1.624 |
| undf | undf | undf | −7.38 | −4.92 | −3.70 | 130.000 | −1.556 |
| 8.53 | undf | undf | undf | −6.98 | −4.81 | 132.000 | −1.494 |
| 6.14 | undf | undf | undf | undf | −6.65 | 134.000 | −1.440 |
| 4.87 | 6.88 | undf | undf | undf | undf | 136.000 | −1.390 |
| 4.08 | 5.34 | 7.75 | undf | undf | undf | 138.000 | −1.346 |
| 3.54 | 4.41 | 5.87 | 8.79 | undf | undf | 140.000 | −1.305 |
| 3.15 | 3.79 | 4.77 | 6.47 | undf | undf | 142.000 | −1.269 |
| 2.85 | 3.34 | 4.06 | 5.17 | 7.15 | undf | 144.000 | −1.236 |
| 2.61 | 3.01 | 3.55 | 4.34 | 5.61 | 7.93 | 146.000 | −1.206 |
| 2.42 | 2.74 | 3.17 | 3.77 | 4.65 | 6.09 | 148.000 | −1.179 |
| 2.26 | 2.53 | 2.88 | 3.35 | 4.00 | 4.99 | 150.000 | −1.155 |
| 2.13 | 2.36 | 2.65 | 3.02 | 3.53 | 4.25 | 152.000 | −1.133 |
| 2.01 | 2.21 | 2.45 | 2.76 | 3.16 | 3.72 | 154.000 | −1.113 |
| 1.91 | 2.08 | 2.29 | 2.55 | 2.88 | 3.31 | 156.000 | −1.095 |
| 1.83 | 1.97 | 2.15 | 2.37 | 2.65 | 3.00 | 158.000 | −1.079 |
| 1.75 | 1.88 | 2.04 | 2.22 | 2.46 | 2.75 | 160.000 | −1.064 |
| 1.68 | 1.79 | 1.93 | 2.09 | 2.29 | 2.54 | 162.000 | −1.051 |
| 1.62 | 1.72 | 1.84 | 1.98 | 2.15 | 2.36 | 164.000 | −1.040 |
| 1.56 | 1.65 | 1.76 | 1.88 | 2.03 | 2.21 | 166.000 | −1.031 |
| 1.51 | 1.59 | 1.68 | 1.80 | 1.93 | 2.08 | 168.000 | −1.022 |
| 1.46 | 1.53 | 1.62 | 1.72 | 1.83 | 1.97 | 170.000 | −1.015 |
| 1.41 | 1.48 | 1.56 | 1.65 | 1.75 | 1.87 | 172.000 | −1.010 |
| 1.37 | 1.43 | 1.50 | 1.58 | 1.67 | 1.78 | 174.000 | −1.006 |
| 1.33 | 1.39 | 1.45 | 1.52 | 1.60 | 1.70 | 176.000 | −1.002 |
| 1.30 | 1.34 | 1.40 | 1.47 | 1.54 | 1.62 | 178.000 | −1.001 |

'undf' = undefined

I claim:

1. A method for making Doppler ultrasound measurements comprising the following steps:

(a) providing an ultrasound probe comprising first and second transducer arrays, each array comprising a respective plurality of transducer elements and a central image plane, said central image planes oriented to intersect at an angle greater than 45°; said arrays spaced from one another;

(b) using the first transducer array to measure a plurality of first apparent Doppler parameters at a respective plurality of regions within a cross-section of a structure; and (c) using the second transducer array to measure a second apparent Doppler parameter substantially at one of the regions.

2. The method of claim 1 wherein steps (b) and (c) are performed to overlap in time.

3. The method of claim 1 wherein the first and second apparent Doppler parameters are indicative of respective apparent Doppler velocities.

4. The method of claim 3 further comprising the step of (d) using the second apparent Doppler parameters measured in step (c) to correct at least some of the first apparent Doppler parameters measured in step (b) to more nearly equal true velocity.

5. The method of claim 4 further comprising the step of:

(e) integrating the corrected Doppler parameters of step (d) to estimate flow rate.

6. The method of claim 5 further comprising the step of:

(f) correcting the flow rate to reduce distortion associated with a non-perpendicular relationship between the true velocity and the cross section.

7. The method of claim 1 wherein the central image planes of the arrays of the probe provided in step (a) are substantially perpendicular to one another.

8. The method of claim 1 wherein each of the transducer elements provided in step (a) is longer in a length direction than in a width direction, wherein each of the transducer elements is aligned along the length direction with a respective element axis; wherein the element axes of the transducer elements of the first transducer array are parallel to one another; wherein the element axes of the transducer elements of the second transducer array are parallel to one another; and wherein the element axes of the transducer elements of the first transducer array are substantially perpendicular to the element axes of the transducer elements of the second transducer array.

9. The invention of claim 8 wherein the transducer elements provided in step (a) are oriented such that, for each of the transducer arrays, the element axes of the transducer array are substantially perpendicular to the central image plane of that transducer array.

* * * * *